US008487620B2

(12) United States Patent
Brown et al.

(10) Patent No.: US 8,487,620 B2
(45) Date of Patent: Jul. 16, 2013

(54) MODULAR APPARATUS FOR MAGNETIC RESONANCE IMAGING

(75) Inventors: Brian Brown, Wauwatosa, WI (US); Steven Wolff, New York, NY (US); Kyle Johnson, Waukesha, WI (US); Glenn Wells, Elm Grove, WI (US); Venkat Goruganti, Pewaukee, WI (US)

(73) Assignee: Neocoil, LLC, Pewaukee, WI (US)

( * ) Notice: Subject to any disclaimer, the term of this patent is extended or adjusted under 35 U.S.C. 154(b) by 494 days.

(21) Appl. No.: 12/816,879

(22) Filed: Jun. 16, 2010

(65) Prior Publication Data

US 2010/0315085 A1 Dec. 16, 2010

Related U.S. Application Data

(60) Provisional application No. 61/187,522, filed on Jun. 16, 2009.

(51) Int. Cl.
*G01V 3/00* (2006.01)

(52) U.S. Cl.
USPC ........................................................ 324/318

(58) Field of Classification Search
USPC .......................... 324/300–322; 600/407–445
See application file for complete search history.

(56) References Cited

U.S. PATENT DOCUMENTS

| | | |
|---|---|---|
| 4,733,190 A | 3/1988 | Dembinski |
| 4,793,356 A | 12/1988 | Misic et al. |
| 4,920,318 A | 4/1990 | Misic et al. |
| 5,594,339 A | 1/1997 | Henderson et al. |
| 6,029,082 A | 2/2000 | Srinivasan et al. |
| 6,498,489 B1 | 12/2002 | Vij |
| 6,591,128 B1 | 7/2003 | Wu et al. |
| 6,611,702 B2 | 8/2003 | Rohling et al. |
| 6,650,926 B1 | 11/2003 | Chan et al. |
| 6,762,606 B2 | 7/2004 | Jevtic et al. |
| 6,867,593 B2 | 3/2005 | Menon et al. |
| 6,992,486 B2 | 1/2006 | Srinivasan |
| 7,378,846 B1 | 5/2008 | Damadian |
| 7,397,245 B2 | 7/2008 | Wohlfarth |
| 7,511,488 B2 * | 3/2009 | Romero et al. ............... 324/303 |
| 7,514,924 B2 * | 4/2009 | Luedeke et al. .............. 324/309 |
| 7,599,728 B2 | 10/2009 | Feenan |

(Continued)

OTHER PUBLICATIONS

International Search Report dated Jan. 26, 2011 for PCT/US2010/038835.

(Continued)

*Primary Examiner* — Brij Shrivastav
(74) *Attorney, Agent, or Firm* — Boyle Fredrickson, S.C.

(57) ABSTRACT

The present invention discloses a modular MRI imaging system. The imaging system includes MRI radio-frequency antenna arrays separate from the patient support structure. The antenna arrays are affixed to a thin, flexible film such that they may be located next to the anatomical region of interest. In addition, multiple antenna arrays may be configured in various planar or three-dimensional arrangements to optimize the FOV and SNR. Separate patient support structures are provided that enhance ergonomics and patient stabilization. By removing the antenna from the housing, the support structures may be designed without the constraints of supporting the antenna or the associated electronics. The MRI imaging system further employs a preamplifier module. The preamplifier module houses the preamplifier and much of the other associated circuitry for each of the antennae. The preamplifier module operates to combine the signals from the antenna arrays and pass the signals to the MRI system.

20 Claims, 13 Drawing Sheets

U.S. PATENT DOCUMENTS

| | | |
|---|---|---|
| 7,602,187 B2 * | 10/2009 | Luedeke et al. ............... 324/318 |
| 7,602,190 B2 | 10/2009 | Piferi et al. |
| 7,834,626 B2 * | 11/2010 | Renz ............................ 324/318 |
| 8,207,737 B2 * | 6/2012 | Greim .......................... 324/322 |
| 2005/0073309 A1 | 4/2005 | Williams et al. |
| 2005/0107686 A1 | 5/2005 | Chan et al. |
| 2005/0113668 A1 | 5/2005 | Srinivasan |
| 2007/0016003 A1 | 1/2007 | Piron et al. |
| 2008/0007250 A1 | 1/2008 | Wiggins |
| 2008/0204021 A1 | 8/2008 | Leussler et al. |
| 2008/0211498 A1 | 9/2008 | Dannels et al. |
| 2008/0284435 A1 | 11/2008 | Overweg et al. |
| 2008/0306377 A1 | 12/2008 | Piron et al. |
| 2009/0088627 A1 | 4/2009 | Piferi et al. |

OTHER PUBLICATIONS

Nordmeyer-Massner, J.A., et al., Mechanically Adjustable Coil Array for Wrist MRI, Magnetic Resonance in Medicine 61, pp. 429-438, 2009, Institute for Biomedical Engineering, ETH and University of Zurich, Zurich, Switzerland.

* cited by examiner

MODULAR APPARATUS FOR MAGNETIC RESONANCE IMAGING

CROSS-REFERENCE TO RELATED APPLICATIONS

This application claims priority to U.S. provisional application Ser. No. 61/187,522, filed Jun. 16, 2009, the entire contents of which is incorporated herein by reference.

BACKGROUND OF THE INVENTION

The subject matter disclosed herein relates to magnetic resonance imaging. More specifically, the subject matter relates to a modular and separable architecture of the radio frequency antenna arrays, the amplifier and channel combination circuitry, and the patient support, or stabilization, devices.

As is known to those skilled in the art, a magnetic resonance image (MRI) detects the faint nuclear magnetic resonance (NMR) signals given off by protons in the presence of a strong magnetic field after excitation by a radio frequency signal. The NMR signals are detected using antennae, commonly referred to as "coils."

Antennae are configured to send signals to the host MRI scanner that enable trained practitioners to make appropriate diagnoses of an anatomical region of interest. For effective imaging, the antennae and their housing take on different shapes due to the shape of the anatomical region of interest. For example, the shape of a housing to fit over a shoulder is necessarily different than the shape of a housing used to image a foot. Similarly, the antennae and housings need to adapt for variations in the size of a particular anatomical region. For example, the same housing sized to fit a pediatric torso will not fit the torso of a large adult. As a result, the antennae and their corresponding housings must be designed to accommodate a broad range of anatomical regions of varying sizes, and imaging centers are required to invest in a significant number of coils to cover all imaging applications. Therefore, it would be desirable to provide an imaging system that reduces the number of sizes and configurations of housings required while servicing the same or an increased breadth of imaging applications.

Patient comfort and stabilization of the anatomy are important while obtaining an MRI because the procedures may last for tens of minutes and require the patient to remain still to prevent motion induced artifacts from appearing in the images. Historically, the antenna housing has served a dual role of stabilizing the anatomical region of interest and providing a support structure for the antennae and their associated electronic components. To assist with patient immobilization, housings have been formed from a rigid plastic to conform to different anatomical regions of interest. To assist with patient comfort, the housings may also include a layer of padding, such as foam, mounted on the support structure at points where the support structure contacts the patient.

However, requirements for designing the housing for patient comfort and for stabilizing the region of interest are often at odds with the requirements for improving the reception of the antennae within the housing. Because the sensitivity of an antenna to the NMR signals transmitted by the body decreases as the separation between the antenna and the body increases, it is desirable to place the antennae as close as possible to the anatomical region of interest, obtaining as high of a signal to noise ratio (SNR) as possible. However, design considerations for the housing to achieve patient comfort and stability impose practical limitations on how close the antennae may be placed to the anatomical region of interest. Therefore, it would be desirable to provide an imaging system that places the antennae close to the anatomical regions of interest without comprising patient comfort and stabilization.

Serviceability of an antenna is another important consideration for selecting an imaging system. If one of the antenna loops or other electrical component in a housing configured for a specific anatomical region were to fail, this housing and the enclosed electrical components must typically be returned to the vendor for repair. Due to the expense of each housing, an imaging center will often have only one of any particular size or configuration of housing. As a result, the imaging center loses revenue and must reschedule patients that would otherwise require that housing during the time it is out for repair. Therefore, it would be desirable to provide an imaging system with modular components at a low enough cost that spare parts may be kept on hand and readily exchanged in the event a component fails.

The ability to upgrade is still another important consideration when selecting an imaging system. The technology for MRI systems is constantly evolving with a trend towards higher channel count and more simultaneous imaging channels. The increased number of channels provides benefits, such as increased parallel imaging, faster scans, and images with higher signal to noise ration. Present imaging systems may have sixteen, thirty-two, sixty-four, or even ninety-six channels, with higher numbers of channels being planned. With the existing antenna and housing structures, the housings need to be upgraded as MRI scanners with higher channel counts are introduced to fully utilize the increased capabilities of the new MRI scanner. Therefore, it would be desirable to provide an imaging system which is scalable so that extra channels may be added as the capabilities of the MRI scanner allow.

SUMMARY OF THE INVENTION

Consistent with the foregoing and in accordance with the subject matter as embodied and broadly described herein, a modular and separable architecture of radio frequency antenna arrays, amplifiers, channel combination circuitry, and patient support, or stabilization, devices for use in MRI imaging is described in suitable detail to enable one of ordinary skill in the art to make and use the invention.

The present invention discloses an MRI radio-frequency antenna arrangement that is separate from the patient support structure. An antenna array includes multiple antenna loops and preferably includes either eight or sixteen loops, functioning as a one of the modular blocks of the present system. The antenna arrays are affixed to a thin, flexible film such that they may be located next to the anatomical region of interest. In addition, multiple antenna arrays may be configured in various planar or three-dimensional arrangements to optimize the field-of-view (FOV) and SNR. The arrays are modular such that additional arrays are readily added to increase the useable field-of-view and to support parallel imaging.

Separate patient support structures are provided that enhance ergonomics and patient stabilization. By removing the antennae from the housing, the support structures may be designed without the constraints of supporting the antennae or the associated electronics. The support structures are designed to provide support and stabilization for a particular anatomical region, but may also be designed to accommodate patients in a range of sizes to minimize the number of support structures required. Providing separate antenna arrays and support structures also allow components to be designed that are typically lighter than previous systems, facilitating transport and setup for imaging.

The MRI imaging system disclosed herein further employs a preamplifier module. The preamplifier module can automatically detect antenna arrays connected at the input connectors and determine how to process the signals to provide outputs sent to the MRI scanner. In addition, the preamplifier module houses the electronic components for the preamplifier circuit for each antenna loop along with signal processing circuitry for processing the signals received from each antenna loop connected to the preamplifier module. Each antenna loop has an electrical conductor connected to the loop by a feed circuit. All of the electrical conductors for an antenna array are bundled together and connected to the preamplifier box. The preamplifier box processes the signals from the antenna arrays, combines the signals if necessary, and passes the signals to the MRI scanner.

According to one embodiment of the present invention, a MRI receiver for detecting a plurality of NMR signals and for transmitting the NMR signals to a MRI scanner includes at least one antenna array. Each antenna array has a flexible substrate and a plurality of antennae mounted on the substrate, each antenna overlapping at least one other antenna. The MRI receiver also includes a cable having a plurality of electrical conductors corresponding to one of the antennae, and a preamplifier module having at least one input connector and at least one output connector. The input connector is configured to receive the cable to connect the preamplifier module to the antenna array, and the output connector is configured to connect the preamplifier module to the MRI scanner. The antenna array may also include a pick-up circuit mounted on the substrate to transfer the NMR signal received on each antenna to the corresponding electrical conductor.

As another aspect of the invention, a first antenna array is connected to a first input connector on the preamplifier module and a second antenna array is connected to a second input connector on the preamplifier module. The preamplifier module combines the signals from the first and second antenna arrays into a combined output transmitted on the output connector to the MRI scanner.

Thus, it is a feature of this invention to provide a modular system for detecting the NMR signals generated during magnetic resonance imaging. The separate antenna arrays allow freedom of placement, such as anterior and posterior positioning of an area to be imaged, to achieve desired coverage of an anatomical region.

As still another aspect of this invention, the antenna array is generally rectangular and may be selectively positioned in a generally planar first state or a generally arcuate second state. A spacer block extending between a first edge and a second edge of the antenna array at a first end of the antenna array is included. The spacer block is configured to be on the outer surface of the antenna array when the antenna array is in the second state and is configured to engage the inner surface of a second end of the antenna array overlapping the first end of the antenna array such that the second end of the antenna array is positioned at an angle to the first end of sufficient magnitude to minimize coupling between overlapping antennae.

Thus, it is another feature of this invention that the antenna array is configured to wrap around an anatomical region to be imaged such that the ends of the antenna array overlap without increasing coupling between overlapping antennae that would result in undesirable image artifacts.

According to yet another aspect of the invention, the MRI receiver may include a stabilization structure. The stabilization structure includes a base plate and a support member adjustably positioned on the base plate. The stabilization structure includes a first mounting surface to which a first end of the antenna array is removably connected, and a second mounting surface to which a second end of the antenna array is removably connected. An angle formed between the first mounting surface and the second mounting surface is of sufficient magnitude to minimize coupling between overlapping antennae.

It is still another aspect of the invention that the MRI receiver may include a shield for radiated emissions removably connected to the stabilization structure. The shield is a radio frequency (RF) blanket, including at least one conductive layer configured to prevent RF signals from radiating therethrough, a flexible outer layer substantially covering the conductive layer, and a fastener attached to the outer layer for connecting the RF blanket to the stabilization structure. The RF blanket may further include at least one absorbing layer covering one of the conductive layers wherein the conductive layer is either a sheet or mesh material.

According to another embodiment of the invention, a MRI receiver for receiving a plurality of NMR signals and for transmitting the NMR signals to a MRI scanner includes a stabilization structure which has a base plate and a support member adjustably positioned on the base plate. At least one antenna array is removably connected to the stabilization structure. Each antenna array includes a flexible substrate and a plurality of antennae mounted on the substrate, each antenna overlapping at least one other antenna. A preamplifier module has at least one input connector and at least one output connector. The input connector is configured to connect the preamplifier module to the antenna array, and the output connector is configured to connect the preamplifier module to the MRI scanner. A cable electrically connects the antenna array to the preamplifier module and has a plurality of electrical conductors corresponding to one of the antennae. The MRI receiver may also include a second stabilization structure adjustably positioned on the base plate These and other objects, advantages, and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWING(S)

Preferred exemplary embodiments of the subject matter disclosed herein are illustrated in the accompanying drawings in which like reference numerals represent like parts throughout, and in which.

Figure 1:
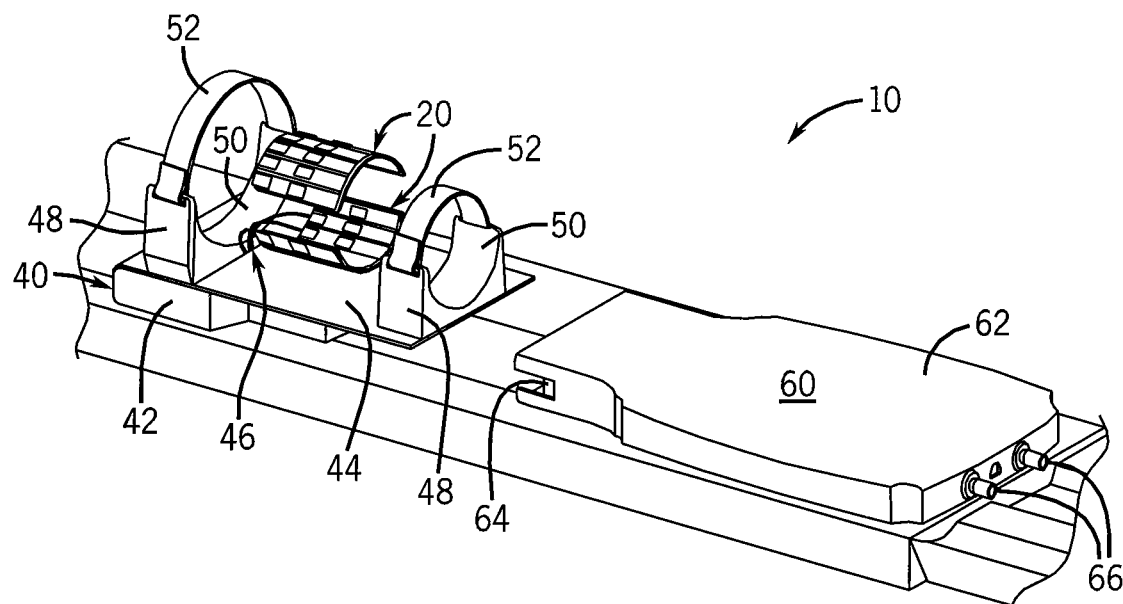
FIG. 1 is an isometric view of one embodiment of the present invention configured to scan a leg of a patient.

In describing the preferred embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terms similar thereto are often used. They are not limited to direct connection but include connection through other elements where such connection is recognized as being equivalent by those skilled in the art.

DETAILED DESCRIPTION OF THE PREFERRED EMBODIMENTS

The various features and advantageous details of the subject matter disclosed herein are explained more fully with reference to the non-limiting embodiments described in detail in the following description.

Figure 2:
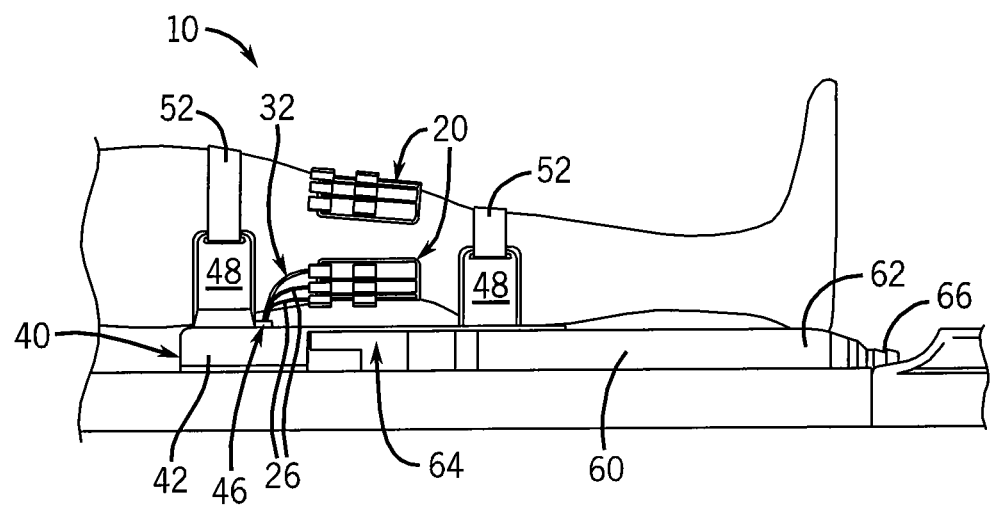
FIG. 2 is a side view of the embodiment of the present invention in FIG. 1.
Figure 3:
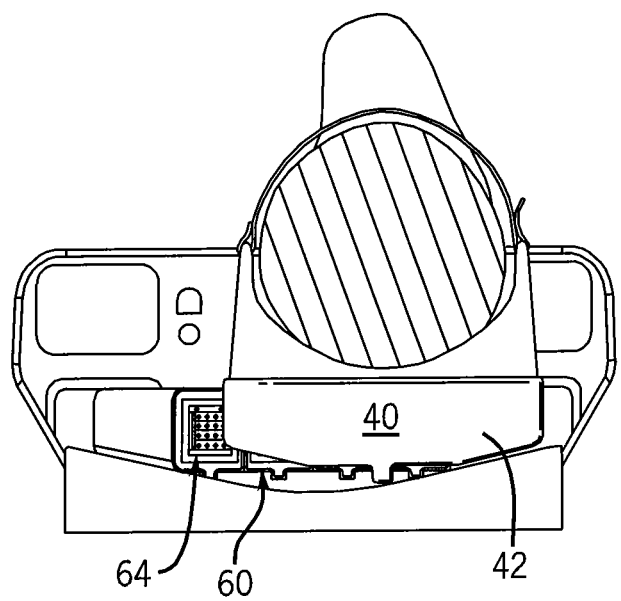
FIG. 3 is a end view of the embodiment of the present invention in FIG. 1.
Figure 4:
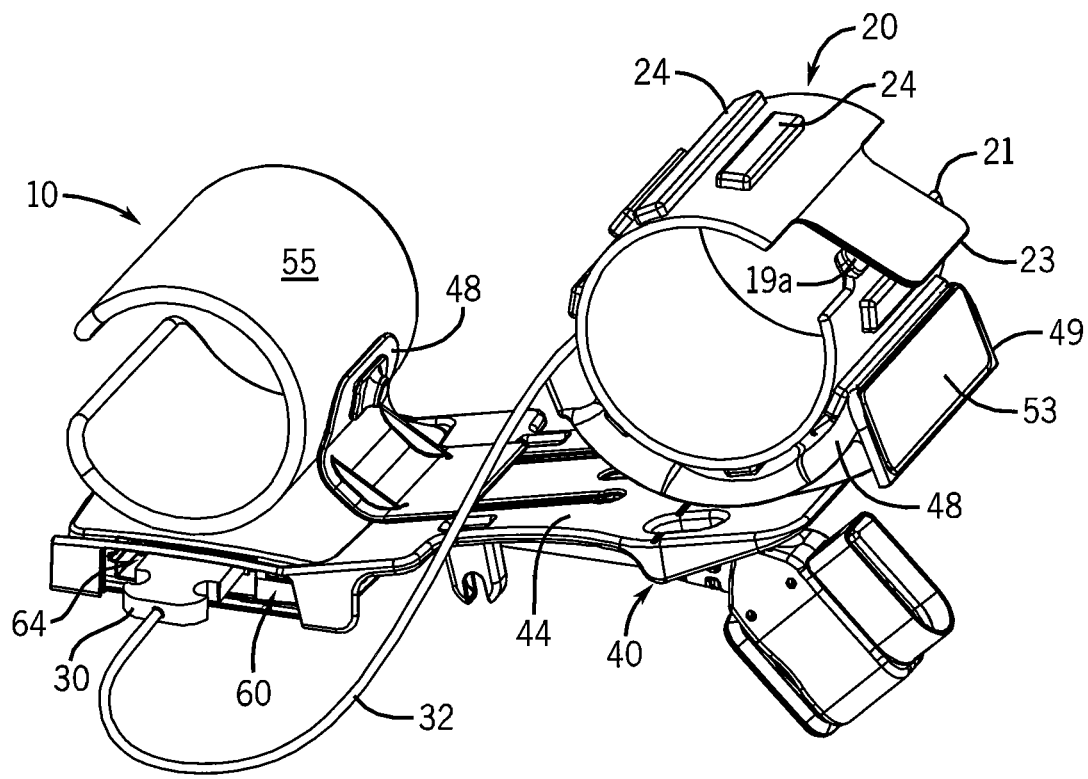
FIG. 4 is an isometric view of another embodiment of the present invention configured to scan a leg of a patient.
Figure 5:
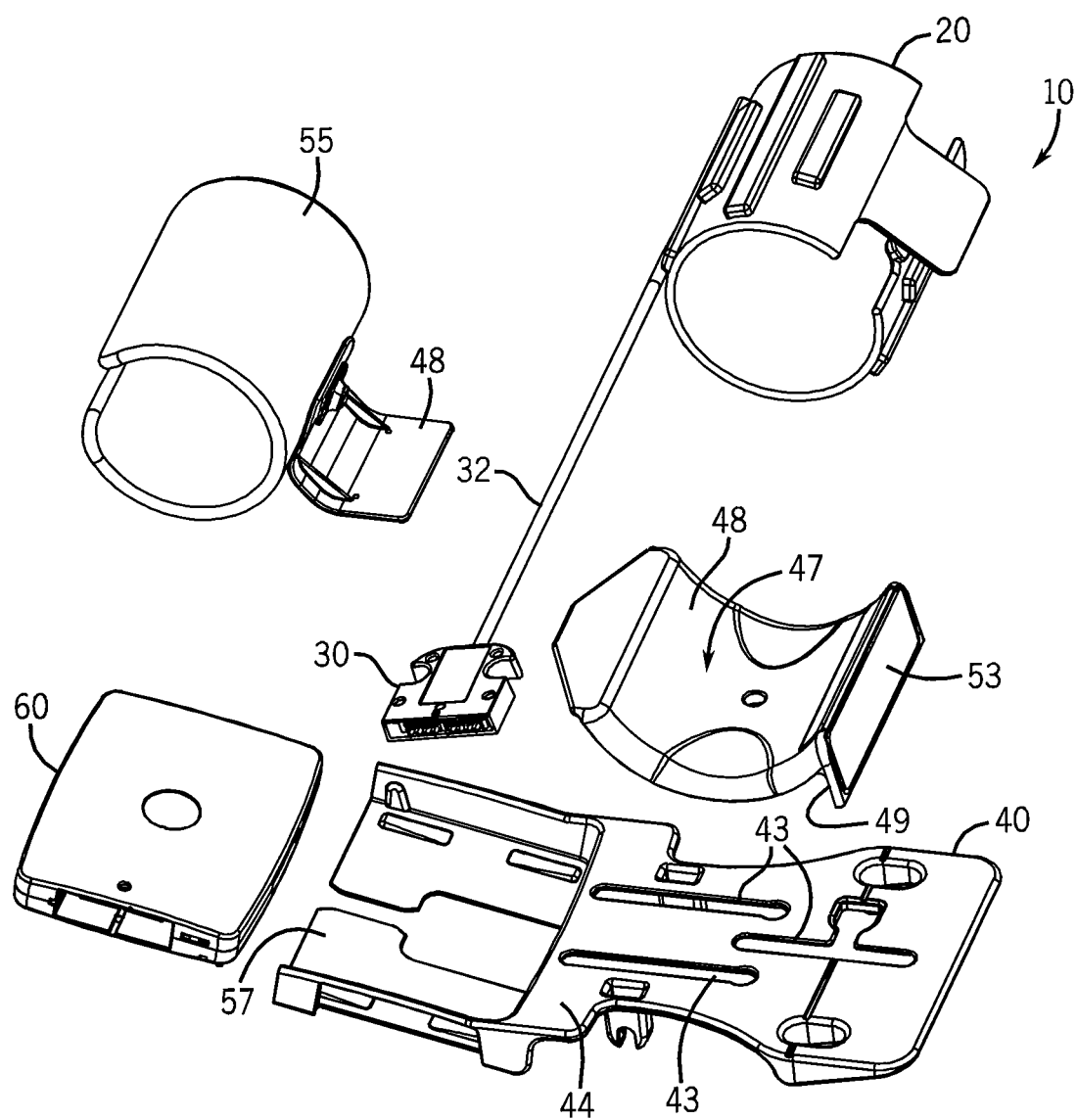
FIG. 5 is an exploded isometric view of the embodiment of the present invention in FIG. 4.

Referring to FIGS. 1-3, a first embodiment of an MM imaging receiver 10 according to the present invention is illustrated. In this embodiment, the imaging receiver 10 is configured to obtain images of a patient's leg and, specifically, the knee. The imaging receiver 10 preferably includes three fundamental components: the antenna arrays 20, the patient stabilization structure 40, and the preamplifier module 60. Each antenna array 20 is a modular structure including multiple antenna loops 22. The antenna arrays 20 preferably include eight, sixteen, or twenty-four individual antenna loops 22 arranged in one or more rows. Each row, for example, may contain eight antenna loops 22. The antenna loops 22 are further arranged such that adjacent loops 22 overlap to reduce mutual coupling between the adjacent loops 22, according to techniques known in the art. The antenna arrays 20 are mounted to a flexible, thin film substrate 28, for example KAPTON®, such that the substrate 28 may be flexed in an arcuate manner positioning the antenna loops 22 around and close to an anatomical region to be imaged. At least one cable 32 is connected to the antenna array 20. Each cable 32 includes at least one conductor 26 carrying the signals from each antenna loop 22. The cables 32 are preferably pre-terminated to a single connector 30 (see, for example, FIG. 4), such that each antenna array 20 may be quickly connected or disconnected as a single unit in the imaging receiver 10. The modular nature of the antenna arrays 20 further allows multiple antenna arrays 20 to be used according to, for example, the requirements of a particular anatomical region to be imaged or the number of channels required by the MRI scanner.

The embodiment shown in FIGS. 1-3, uses two, sixteen-loop arrays 20. A first array 20 is positioned on the anterior side of the knee and a second array 20 is positioned on the posterior side of the knee. Each antenna array 20 is curved around the respective surface of the knee such that the array 20 is positioned in close proximity to the area to be scanned. The conductors 26 are gathered together into a cable 32 and pass through an opening 46 in the stabilization structure 40. The opening 46 may be a hole sized to permit a connector 30 attached to the antenna array 20 to pass through. Optionally, the opening 46 may be a slot, extending to one edge of the lower housing 42, in which the cable 32 may be inserted. The cables 32 extend through a cavity within a lower housing 42 on the stabilization structure 40 to a connector portion of the stabilization structure 40. The connector portion may have the cables 32 from the antenna array 20 plug into a mating connector on the stabilization structure 40, which, in turn, plugs into the preamplifier module 60. Alternately, the connector portion on the stabilization structure 40 may provide a means by which the connectors 30 on the cables 32 from the antenna array 20 are held in place by the stabilization structure 40, for example by a clip, tab, pin, or other retaining means, such that the connector 30 may be directly connected to the preamplifier module 60. As still another option, the connector 30 may pass through the lower housing 42 without being secured to the lower housing 42 and connect directly to the preamplifier module 60.

Figure 12:
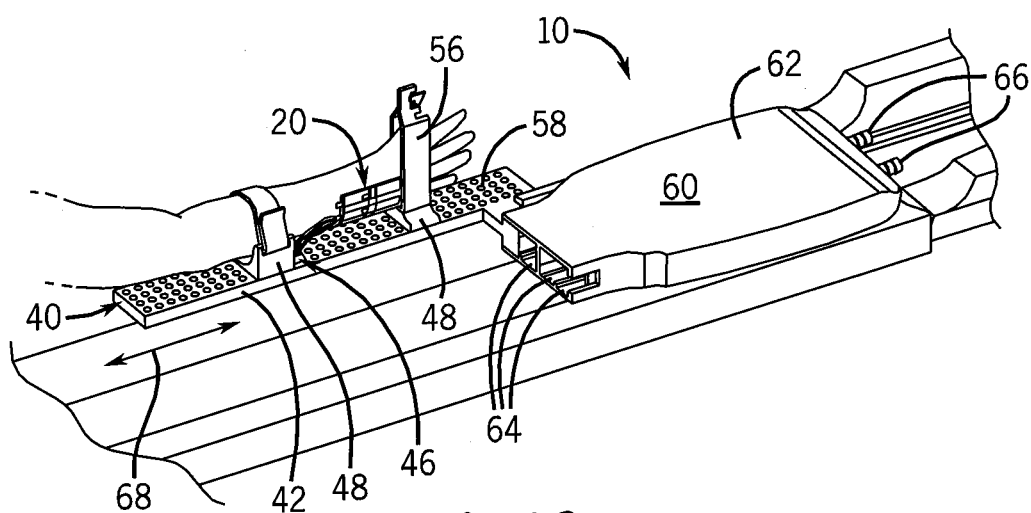
FIG. 12 is an isometric view of another embodiment of the present invention configured to scan an arm of a patient.

The patient stabilization structure 40 shown in FIGS. 1-3, is configured to both provide support to the leg and to help prevent movement of the leg, and particularly the knee, during imaging. The stabilization structure 40 includes a lower housing 42 configured to rest on the MRI table. A base plate 44 is secured to the upper surface of the lower housing 42. Alternately, the base plate 44 may be integrally formed with the lower housing 42. The base plate 44 includes the opening 46 through which the cabling from the antenna arrays 20 may be passed. The base plate 44 may further include an array of mounting holes 58, as seen in FIG. 12. The patient stabilization structure 40 is removably connected to the preamplifier module 60 by aligning and inserting the connector portion of the patient stabilization structure 40 with the input connectors 64 on the preamplifier module 60.

The patient stabilization structure 40 further includes at least one and preferably two support members 48. The bottom surface of the support members 48 is generally flat such that it rests on the upper surface of the base plate 44 and further includes mounting pegs (not shown) extending from the bottom surface of the support member 48. The mounting pegs on the support members 48 may be inserted into the array of mounting holes 58 on the base plate 44 such that the support members 48 may be positioned on the base plate 44 in a configuration to best support the anatomical region of interest, for example the leg of the patient. The support member 48 further includes a pair of sides generally opposed to each other and extending away from the base plate 44. A curved upper surface connects the two side surfaces with the curve of the upper surface extending downward into the support member 48. The support member 48 may be produced in varying sizes to accommodate different sized patients as well as different portions of the anatomical region of interest. FIGS. 1-3 illustrate two such sizes, configured to support the upper and the lower portion of a leg. Each of the support members 48 preferably includes a pad 50 inserted within the curved upper surface. The pad 50 provides support and comfort to the patient. Pads 50 of varying thicknesses may be provided to adjust the inner radius of the curved surface to better accommodate patients of varying sizes.

The support member 48 additionally includes a patient securing portion. For example a strap 52 connected to the support member 48 extends over the leg to secure the leg within the support member 48. The strap 52 may be removably connected from one or both sides of the support member 48 to assist entry and exit of the patient. The strap 52 may be fastened by any means known in the art to provide an adjustable length, for example using a hook and loop fastener, such that the strap 52 securely contacts the patient and generally restricts motion of the leg with respect to the support member 48.

One or more preamplifier modules 60 are used in the imaging receiver 10 to transfer the signals from the antenna arrays 20 to the MRI scanner. The preamplifier module 60 may rest on and optionally be secured to either the MRI table or the patient stabilization structure 40. The preamplifier module 60 may further be covered by or enclosed within an outer layer for further patient support and/or comfort. For example, a foam pad (not shown) may be placed on the upper surface of the preamplifier module 60 to support a portion of the patient's body, such as the foot. Alternately, the preamplifier module 60 may be enclosed within a portion of the housing configured to support a portion of the patient, for example the patient's legs. The preamplifier module 60 includes at least one input connector 64. Each input connector 64 is configured to receive the input signals from an antenna array 20. The preamplifier module 60 further includes one or more output connectors 66. Each output connector 66 is configured to provide signals to the MRI scanner. The preamplifier module 60 may further be configured to combine the input channels into a lower number of output channels. For example, multiple antenna arrays 20 may be used to provide sixty-four channels of input to the preamplifier module 60. However, the MRI scanner may be designed to receive only thirty-two channels of input. The preamplifier module 60 can convert the higher number of input channels to the appropriate number of output channels. In addition, the preamplifier module 60 may auto-detect which input connector 64 has a connector 30 from an antenna array 20 plugged into it and may also read an antenna array identification (ID) from the connector 30. The preamplifier module 60 may similarly auto-detect which physical stabilization structure 40 is connected. The preamplifier module 60 performs processing on the input signals according to which type of antenna array 20, patient stabilization structure 40, or combination thereof is connected to the preamplifier module 60.

Referring next to FIGS. 4-11, another embodiment of an MRI imaging receiver 10 according to the present invention is illustrated. In this embodiment, the imaging receiver 10 is again configured to obtain images of a patient's leg and, specifically, the knee. The imaging receiver 10 includes an antenna array 20 and a preamplifier module 60. The antenna array 20 and preamplifier module 60 may each be removably connected to a patient stabilization structure 40.

Figure 21:
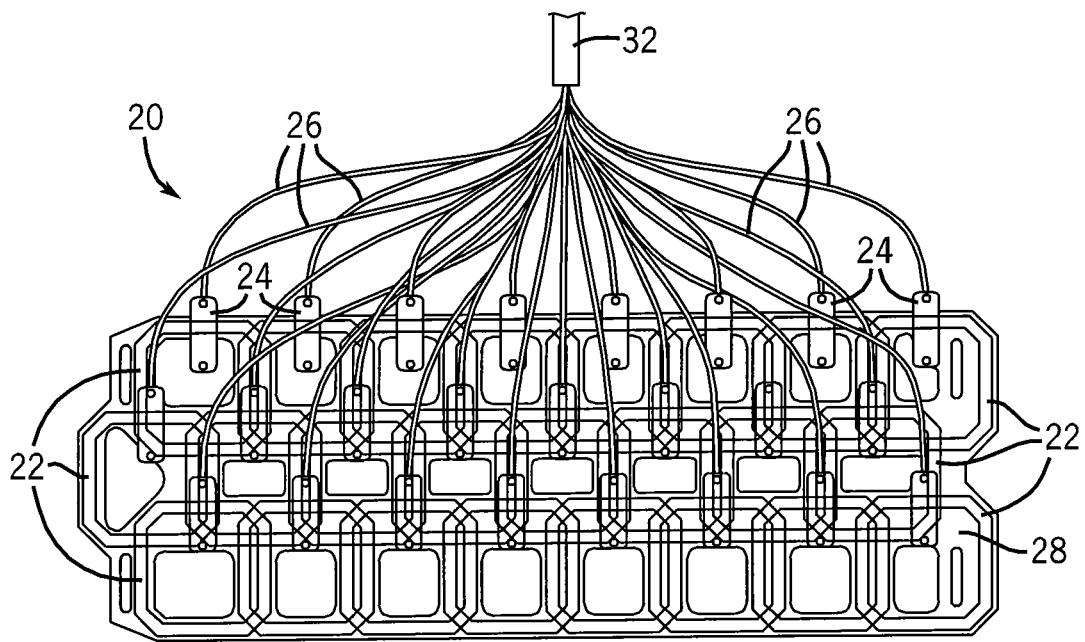
FIG. 21 is an exemplary embodiment of an antenna array according to the present invention.

In this embodiment, a single antenna array 20 is used and wraps around the anatomical region to be imaged. The antenna array 20 may be, but is not limited to, a sixteen-loop array. The antenna loops 22 are arranged such that adjacent loops 22 overlap to reduce mutual coupling. Any suitable arrangement of rows, and numbers of loops 22 per row, may be used to form the antenna array 20. For example, the antenna array 20 may have three rows of antenna loops 22 including five loops 22 in the first and third rows with six loops 22 in the second row. Referring also to FIG. 21, each antenna loop 22 is mounted to a flexible, thin film substrate 28. Pick-up circuits 24 are similarly mounted on the substrate 28 and connected to each antenna loop 22. Preferably, one pick-up circuit 24 exists for each antenna loop 22. However, it is contemplated that a single circuit may include multiple channels, receiving signals from multiple antenna loops 22. A conductor 26 is connected to each pick-up circuit 24 to transmit the NMR signals received by each loop 22 from each pick-up circuit 24 to the preamplifier module 60. All of the conductors 26 are bundled into a cable 32 that is pre-terminated to one or more connectors 30 and removably connected to one or more input connectors 64 on the preamplifier module 60.

Figure 6:
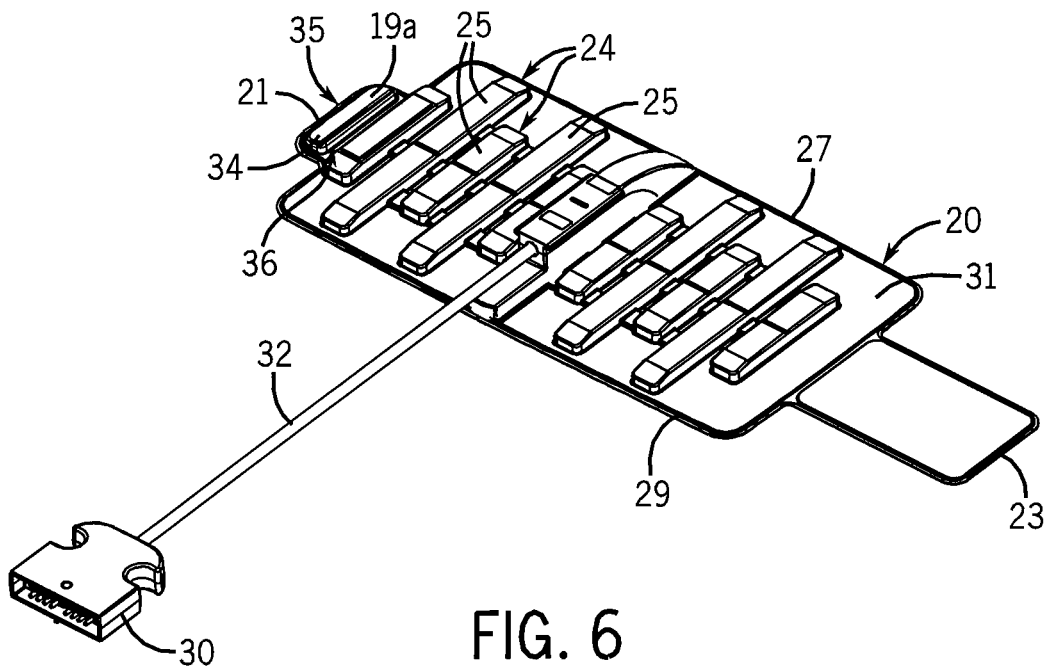
FIG. 6 is an isometric view of the antenna array in FIG. 4.

The antenna array 20 may also include a protective cover 25 for each of the pick-up circuits 24. As illustrated in FIG. 6, the protective cover 25 is preferably elongated and may be configured to extend between a first side 27 and a second side 29 of the antenna array 20. The pick-up circuits 24 and the corresponding protective covers 25 are spatially separated along the length of the array 20 to interface with each antenna loop 22. The protective covers are preferably constructed of a rigid material to provide lateral stability in the antenna array 20. As a result, the protective covers 25 restrict side-to-side flexing of the array 20 while permitting the array 20 to be flexed along the length of the array 20, curving a first end 21 of the array back to a second end 23 of the array in an overlapping manner. It is contemplated that the protective covers 25 may be arranged in other suitable shapes or configurations, and, optionally, separate protective covers and lateral support members may be provided in the array 20.

The antenna array 20 further includes a protective outer layer 31. The outer layer 31 preferably covers the substrate and antenna loops 22. Optionally, the outer layer may also cover the protective covers 25. The outer layer 31 may be a foam layer to provide additional comfort to the patient during imaging.

Because the antenna array 20 wraps around the region being imaged, the antenna array 20 preferably includes a fastener 19, including but not limited to a hook and loop fastener, to secure the first end 21 of the array to the second end 23 of the array. The outer surface of the first end 21 includes one of the hook or loop portions 19*a* of the fastener and the inner surface of the second end 23 includes the other of the hook or loop portions 19*b*. The second end 23 of the array may also include a tab 33 extending longitudinally from the array 20 across at least a portion of the width of the array 20. The hook or loop portion 19*b* of the second end 23 may similarly be placed along the inner surface of the tab 33 such that the array 20 may be overlapped by a varying amount, resulting in a varying diameter curvature to the array 20. Optionally, any suitable fastening means for use in conjunction with an MRI scanner may be used.

Figure 7:
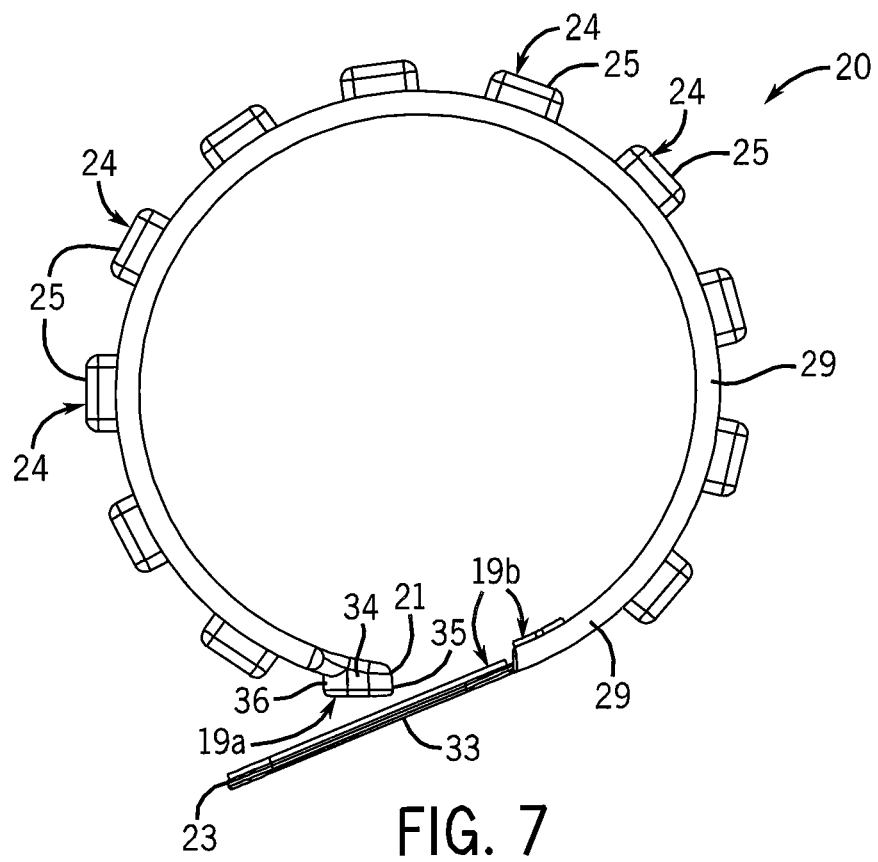
FIG. 7 is a side elevation view of the antenna array in FIG. 4.
Figure 8:
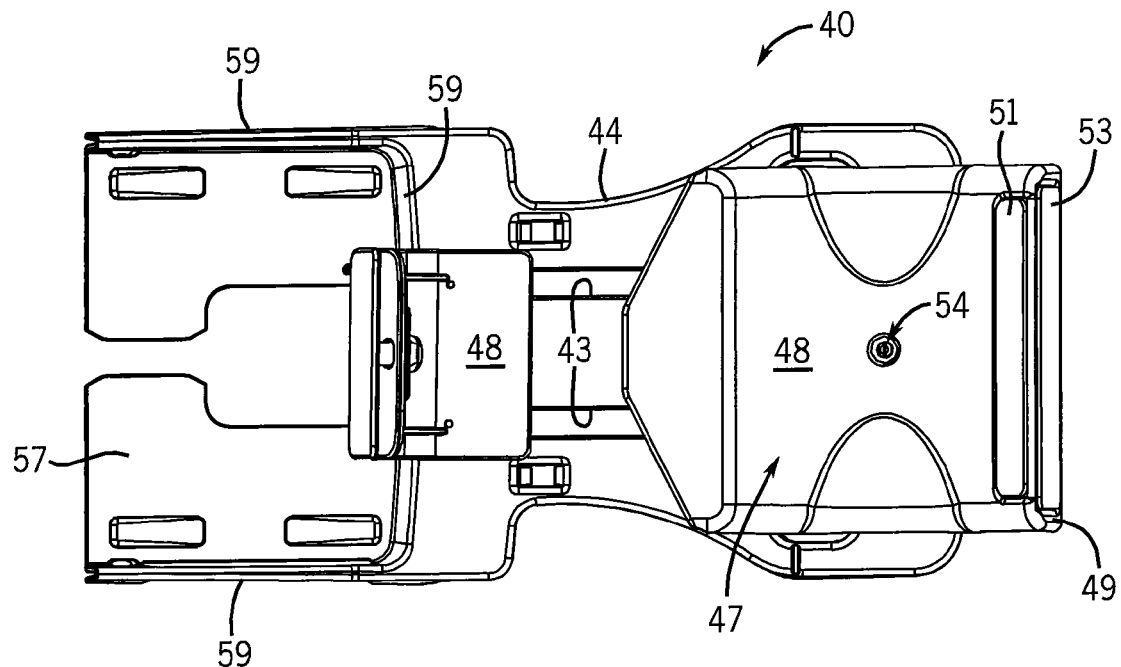
FIG. 8 is a top plan view of the patient stabilization device of FIG. 4.
Figure 9:
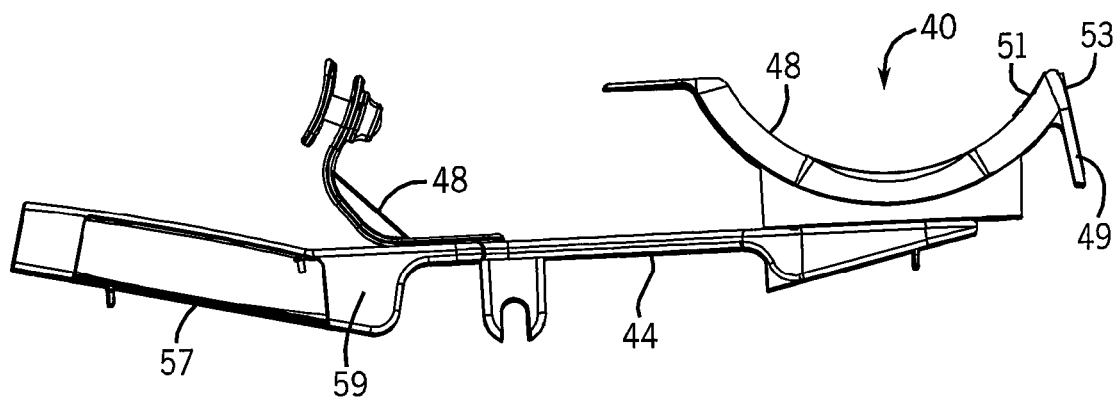
FIG. 9 is a side elevation view of the patient stabilization device of FIG. 4.

The antenna array 20 further includes at least one spacer block 34. As seen in FIG. 7, the spacer block 34 is preferably located at the first end 21 of the array, and the hook and loop fastener 19a may be placed on the outer surface of the spacer block 34. The spacer block 34 has a generally trapezoidal cross-section. The cross-section is narrowest along a first edge 35 of the spacer block 34, positioned nearest the first end 21 of the array 20, with a gradually increasing thickness to a second edge 36 of the spacer block 34. The thickness of the spacer block 34 is selected to minimize coupling between overlapping antenna loops 22, increasing as the size of the antenna loops 22 increases.

The patient stabilization structure 40 includes a base plate 44 and at least one support member 48. The support member 48 positions and provides stability to the anatomical region to be imaged. The support member 48 is preferably curved such that the anatomical region being imaged, for example a leg or an arm, is supported within the curved surface. A pad 47 may also be provided on the curved surface to increase the comfort of the patient.

As previously discussed, the antenna array 20 may include a fastener 19 to secure the first end 21 of the array to the second end 23 of the array. When the antenna array 20 is used in cooperation with the patient stabilization structure 40, a first mating portion 51, corresponding to the hook or loop portion 19a on the antenna array 20, is positioned on the inner curved surface of the support member 48. The first end 21 of the antenna array 20 may then be removably connected to the support member 48 by attaching the hook or loop portion 19a to the first mating portion 51. The support member 48 also includes a mounting plate 49 which may either be connected to or integrally formed with the support member 48. A second mating portion 53, corresponding to the hook or loop portion 19b on the antenna array 20, is positioned on the mounting plate 49 of the support member 48. The second end 23 of the antenna array 20 may then be removably connected to the mounting plate 49 by attaching the hook or loop portion 19b to the second mating portion 53. The mounting plate 49 is further oriented at a sufficient angle to the curved surface of the support member 48, providing sufficient separation between overlapping antenna loops 22 to prevent coupling between the loops 22 in a manner similar to the spacer block 34 discussed above.

The support member 48 may also be variably positioned on the base plate 44. A hub 54 extends away from the support member 48 and engages an elongated opening 43 in the base plate 44 such that the support member 48 is slidably positioned along the opening 43. The hub 54 may be spring-biased, such that a force applied to the support member 48 in the direction of the base plate 44 permits the support member to slide along the opening 43. Removing the force permits the spring to bias the outer edges of the hub 54 against the base plate 44 at the edges of the opening 43, positively retaining the support member 48 in position along the opening 43. Optionally, any other securing means may be used to secure the support member 48 along the opening 43, including, but not limited to, a threaded portion on the hub and a nut. The hub 54 further permits the support member 48 to rotate about the hub with respect to the base plate 44, providing an additional degree of alignment with a patient's body for increased patient comfort.

The patient stabilization structure 40 may further include a second support member 48. The second support member 48 slidably engages the base plate 44 along one or more openings 43 and may be used, for example to support the leg of the patient which is not being imaged. The second support member 48 may further be configured to accept optional accessories to be mounted thereto including, but not limited to, additional padding for patient comfort or a shield for radiated emissions such as a radio frequency (RF) blanket 55 to prevent image wrap around from occurring. Image wrap around occurs when the antenna array 20 detects NMR signals generated from an area outside of the desired field of view (FOV), for example, a leg not being imaged. The RF blanket 55 prevents transmission of radiated emissions between the area covered by the blanket and the antenna array 20. The RF blanket 55 may include, for example, one or more conductive layers, such as copper, which may be either a solid surface or fine mesh, and one or more absorptive layers. The RF blanket 55 also includes a flexible outer layer substantially covering the conductive and absorptive layers and a fastener attached to the outer layer. The fastener may be a hook and loop fastener and removable connect the RF blanket 55 to the second support member 48. Optionally, the RF blanket 55 may be integrally formed with the patient stabilization structure 40.

A cavity 57 is integrally formed in the patient stabilization structure 40 to receive the preamplifier module 60. Walls 59 extend upward around at least a portion of the periphery to positively retain the preamplifier module 60 within the cavity 57. A portion of the periphery of the cavity 57 is preferably open to slidably receive the preamplifier module 60. Optionally, walls 59 may extend upward around the entire periphery and the preamplifier module 60 may be inserted through an open top side of the cavity 57. Openings in the walls 59 provide access to the preamplifier module 60, for example, to connect cables to the input connector 64 and output connector 66 of the preamplifier module 60.

According to yet another feature of the invention, the patient stabilization structure 40 is pivotally mounted, for example, to the table of an MRI scanner. The patient stabilization structure 40 may be rotated plus or minus one hundred eighty degrees to facilitate imaging of either the right or left anatomy.

Figure 13:
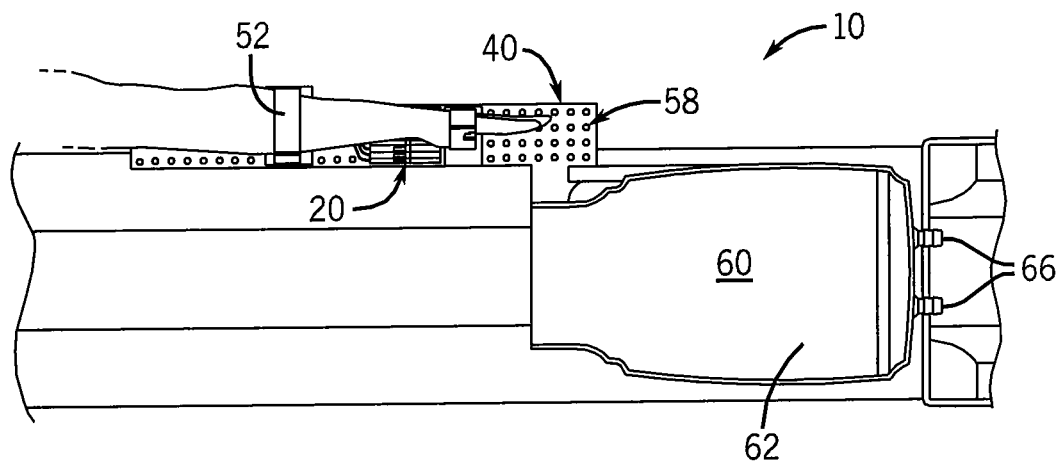
FIG. 13 is a top view of the embodiment of the present invention in FIG. 12.
Figure 14:
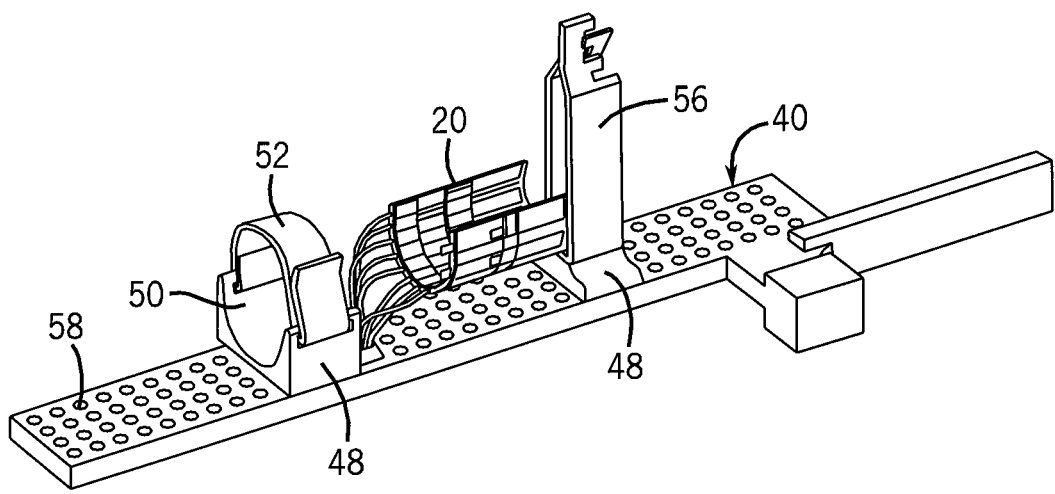
FIG. 14 is an isometric view of the coil array and patient stabilization device in FIG. 12.

Referring to FIGS. 12-14, another embodiment of an MRI imaging receiver 10 according to the present invention is illustrated. This embodiment of the imaging receiver 10 is configured to obtain images of a patient's arm and, specifically, the wrist. The lower housing 42 of the patient stabilization structure 40 is configured to be offset from the preamplifier box such that it may comfortably support and stabilize an arm of a patient which would be oriented along or overhanging the edge of an MRI table. A connector portion of the patient stabilization structure 40 plugs into one of the leftmost or the rightmost connectors on the preamplifier box. A first portion of the housing extends generally perpendicular to the axis of insertion 68 to the preamplifier box and towards the edge of the table. A stabilizing portion of the housing extends generally parallel to and along the side of the preamplifier box. The stabilizing portion rests on the table and contacts the preamplifier box to reduce rotational forces exerted on the connector when a patient's arm is placed on the stabilization structure 40. The main portion of the lower housing 42 connects to the first portion of the housing and extends generally parallel to the axis of insertion 68 of to the preamplifier box and along the MRI table. The lower housing 42 encloses a cavity through which the cable 32 from the antenna array 20 may be directed to the connector portion of the patient stabilization structure 40.

At least one surface of the lower housing 42 includes an array of mounting holes 58. The mounting holes 58 may be included in a base plate 44 secured to the lower housing 42 or alternately the mounting holes 58 may be integrally molded into the lower housing 42. Preferably both surfaces of the lower housing 42 include the array of mounting holes 58 such that one patient stabilization structure 40 may be configured to be inserted into either the leftmost or the rightmost connector on the preamplifier module 60 and have the mounting holes 58 on the upper surface of the lower housing 42.

The embodiment illustrated in FIGS. 12-14 includes two support members 48. A first support member 48 is shown which is identical in construction to the support member 48 disclosed for the leg. The modular nature of the support members 48 permits them to support either an arm or a leg. Depending on the region of anatomical interest to be scanned, two of the first support structures may be used to stabilize the upper and the lower portion of the arm, permitting the elbow to be imaged. Alternately, as illustrated in FIGS. 12-14, the wrist may be the region to be scanned and a second support member 48 to support the hand may be provided. The bottom surface of the second support members 48 is generally flat such that it rests on the upper surface of the lower housing 42 or base plate 44 and further includes mounting pegs (not shown) extending from the bottom surface of the support member 48. The mounting pegs on the second support member 48 may be inserted into the array of mounting holes 58 on the base plate 44 and positioned on the base plate 44 in a configuration to best support the arm or hand of the patient.

A pair of hand retaining members 56 is connected to the upper surface of the second support member 48. The main body of each retaining member 56 is generally rectangular in shape and includes a tab portion at the distal end of the retaining member 56. The retaining members 56 extend upward from the support member 48 and generally opposing each other. The tab portion of each retaining member 56 interlocks the tab portion of the other retaining member 56 to secure the retaining members 56 around the hand of a patient. Alternately, any means of connecting the two retaining members 56 around the hand of a patient suitable for use in an MRI scanner as is known in the art may be used.

Due to the modular nature of the system, the antenna array 20 described previously for imaging a patient's leg may also be used to image a patient's arm. In this embodiment, a single antenna array 20 is positioned generally around the side of the wrist oriented towards the base plate 44 of the stabilization structure 40 and extending around to the front and rear of the wrist. The conductors 26 from the antenna array 20 are gathered together to form a cable 32 and pass through an opening 46 in the lower housing 42. The opening 46 is preferably sized to permit a connector 30 attached to the antenna array 20 to pass through. Alternately, the opening 46 may be a slot extending to one edge of the lower housing 42 and sized to permit the cable 32 to be inserted. The cables 32 extend through the cavity in the lower housing 42 to the connector portion. The cable connector 30 may alternately be joined to the preamplifier module 60 through a mating connector attached to the lower housing 42 or by securing the cable connector 30 in the lower housing 42 such that it is oriented in the connector portion to engage the preamplifier module 60.

Figure 15:
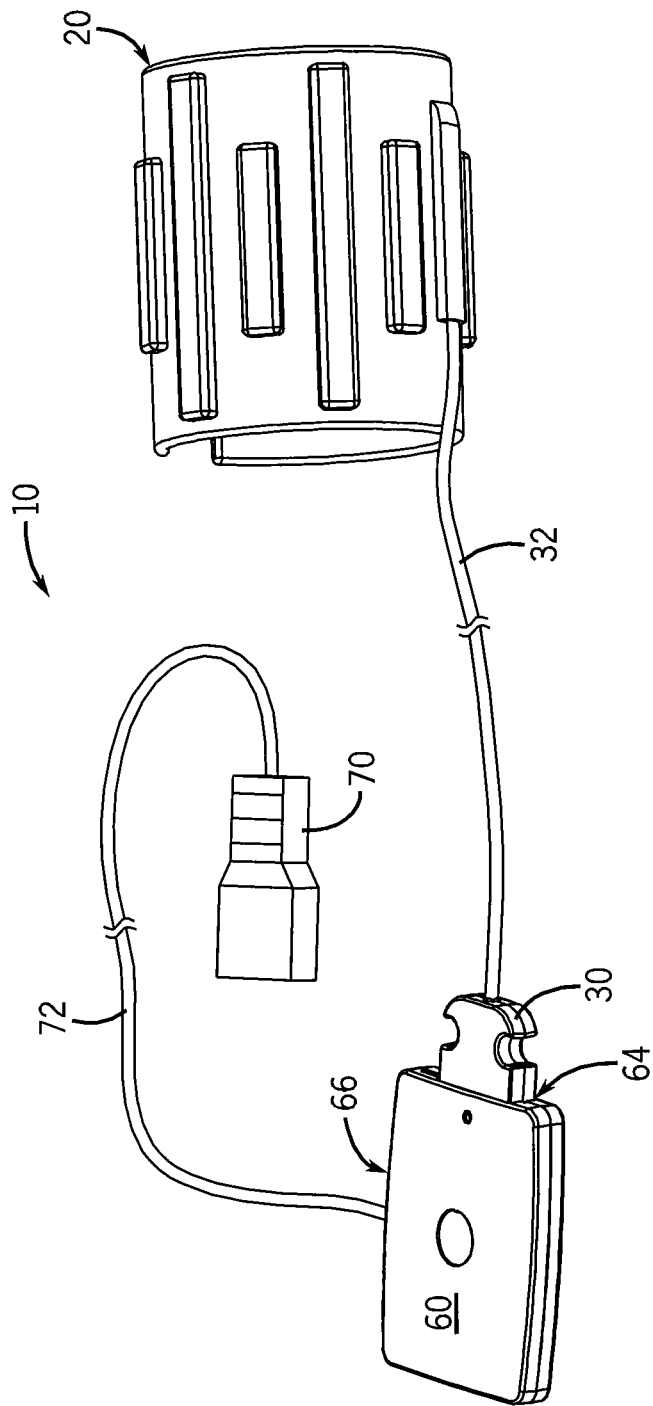
FIG. 15 is an isometric view of another embodiment of the present invention configured to scan an arm of a patient.

Referring next to FIG. 15, another embodiment of an MRI imaging receiver 10 according to the present invention is illustrated. In this embodiment, the imaging receiver 10 is again configured to obtain images of a patient's arm and, specifically, the wrist. The antenna array 20 and preamplifier module 60 as discussed previously with respect to imaging a leg may be used independent of a patient stabilization structure. Other stabilization methods as known in the art, for example sand bags placed along either side of the arm may be used in cooperation with the imaging receiver 10. The preamplifier module 60 may be positioned next to or overhead of the patient as is convenient to provide a connection between the antenna array 20 and the MRI scanner. Optionally, one or more antenna arrays 20 may be used with one or more preamplifier modules 60, the antenna arrays 20 curved or laid flat against the anatomical region to be imaged, as required to obtain the desired image.

Figure 16:
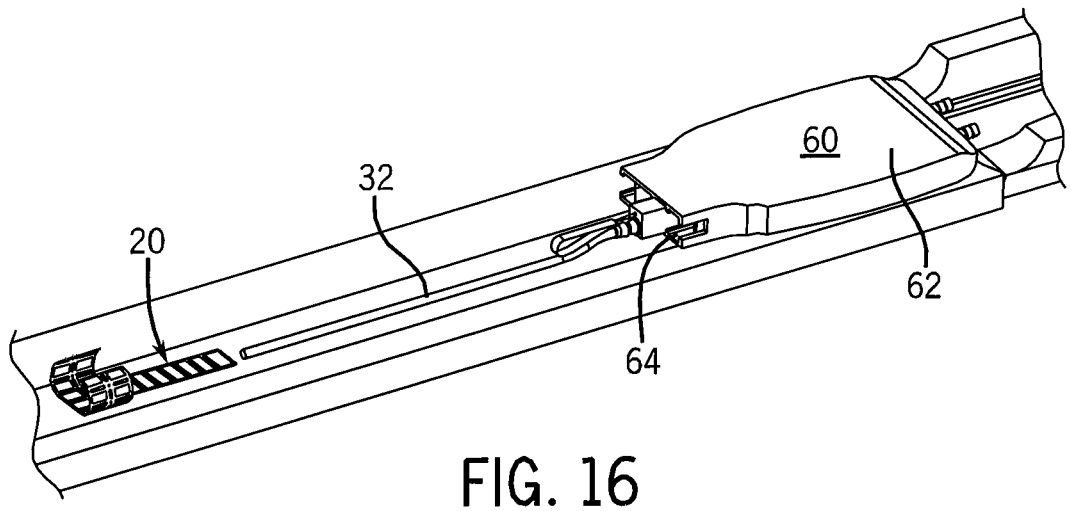
FIG. 16 is an isometric view of another embodiment of the present invention configured for a smaller anatomical region or a pediatric head, neck, and spine.
Figure 17:
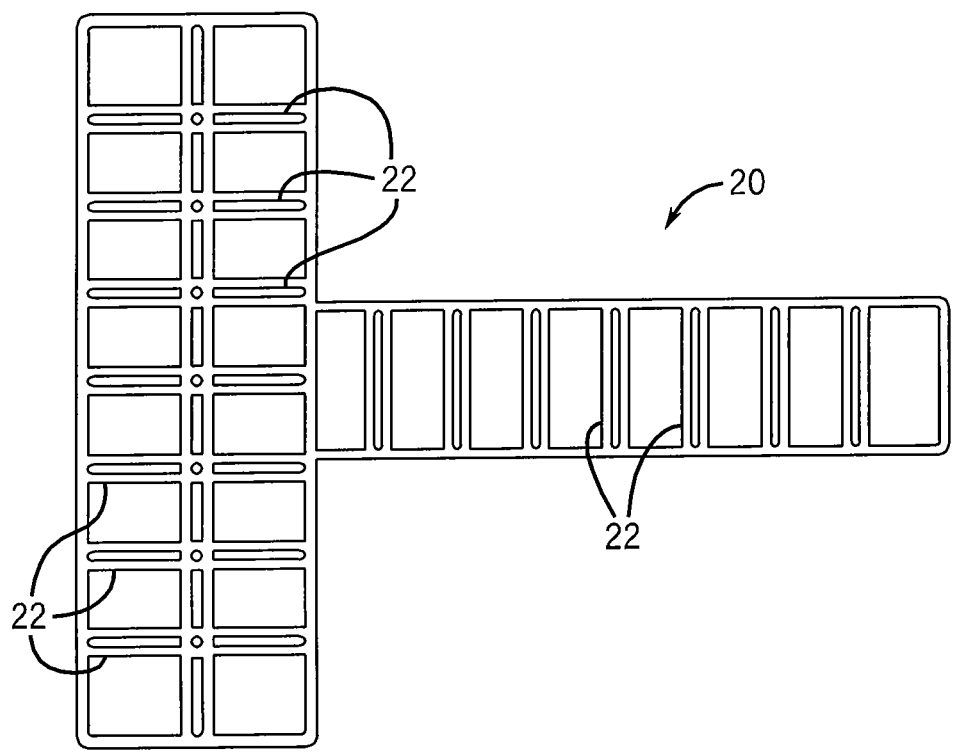
FIG. 17 is an top view of the coil array shown in FIG. 16 and laid flat.

Referring to FIGS. 16-17, another embodiment of an antenna array 20 for use in the MM imaging receiver 10 is disclosed. The antenna array 20 of FIGS. 16-17 is preferably used for imaging the head, neck, and spine of pediatric patients. A first row comprised of multiple antennae form a spinal array configured to be placed under and extending along the spine of the patient. Alternately, the spinal array may be formed from multiple rows of antenna coils. At one end of the spinal array, the conductors 26 from each antenna loop 22 are combined to form a cable 32 extending to the preamplifier module 60. At the other end of the spinal array, a second array of antenna coils is connected.

The second array of antenna coils is preferably connected to the spinal array such that the two arrays form a "T" shape. The second array of antenna loops 22 is illustrated as including two rows of eight antenna loops 22. Alternately, the second array may include any suitable configuration, such as a single row or additional rows of antenna loops 22 of varying numbers of antenna loops 22. The second array is configured to be curved upward around the head of a patient. It is contemplated that the pediatric antenna array 20 may be made of multiple arrays 20 integrally formed into a "T" shape or, alternately, multiple, separate antenna arrays 20 may be positioned to form a "T" shape. The pediatric antenna array 20 is used in coordination with an appropriate stabilization structure 40 to provide simultaneous images of the head, neck and spinal region of a patient.

Figure 18:
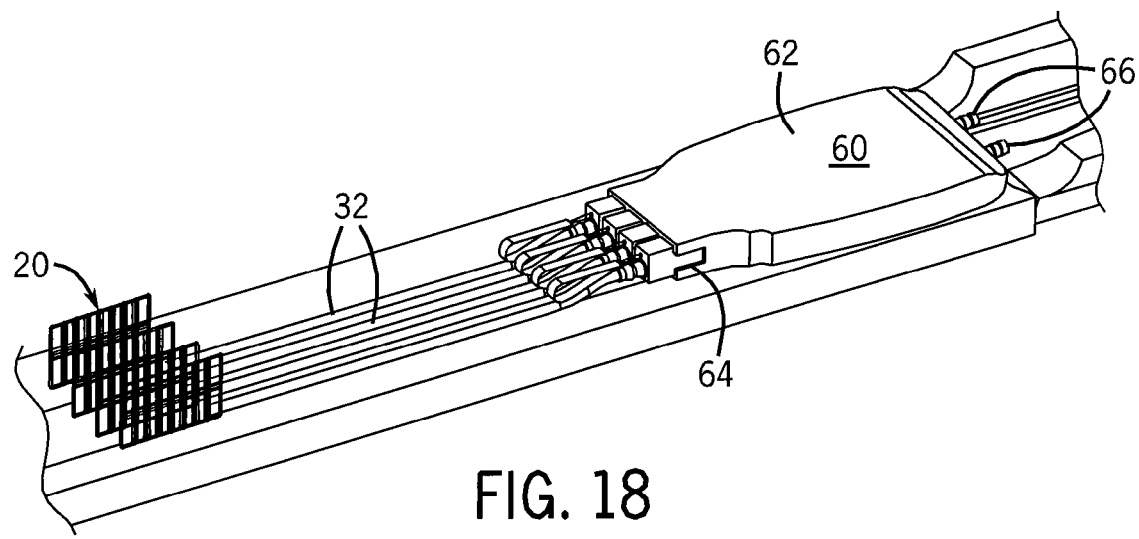
FIG. 18 is an isometric view of another embodiment of the present invention configured to scan breast tissue of a patient.
Figure 19:
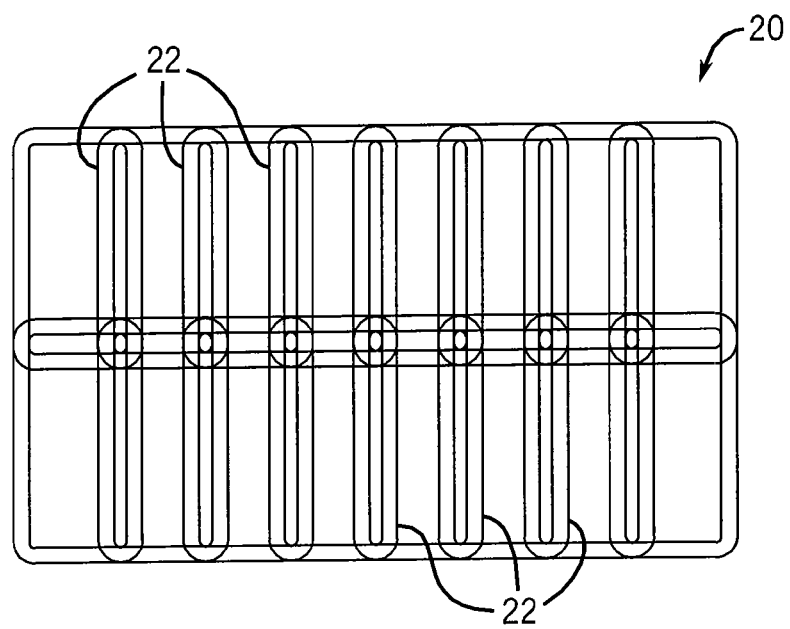
FIG. 19 is a side view of one of the coil arrays in FIG. 18.
Figure 20:
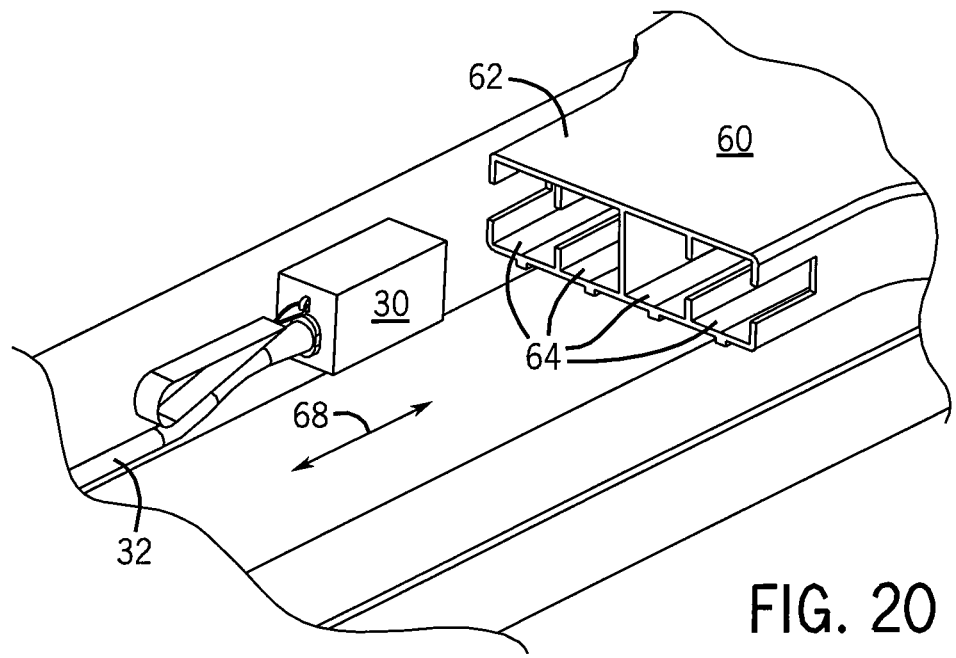
FIG. 20 is an isometric view of the connector between the cable and the preamplifier box in FIG. 18.

Referring to FIGS. 18-20, another embodiment of a series of antenna arrays 20 configured for use in imaging breast tissue is disclosed. Four antenna arrays 20 are provided. The antenna arrays 20 are used along with an appropriate stabilization structure 40 such that one array 20 is placed on each side of a breast. Optionally, a single antenna array 20, wrapped around the chest of the patient, or two antenna arrays, one positioned around each breast, may be used along with an appropriate stabilization structure 40 to image the breast tissue. In FIG. 17, each antenna array 20 includes two rows of antenna loops 22 although any suitable antenna array 20 may be used. A cable 32 extends from one end of antenna array 20 and may be directly connected to a preamplifier module 60. Each array 20 may be connected to a different input connection of the preamplifier module 60 or, optionally, to an input connection of different preamplifier modules 60. Although, each of the above-described configurations preferably permits both breasts to be simultaneously imaged, the antenna arrays 20 may also be arranged to image a single breast.

Referring to FIG. 21, an exemplary embodiment of an antenna array 20 is disclosed. The illustrated antenna array 20 includes three rows of antenna loops 22, each row having eight antenna loops 22. It is contemplated that the antenna array 20 may have varying numbers of rows of antenna loops 22 and varying numbers of loops 22 within each row. The antenna loops 22 are arranged such that adjacent loops 22 overlap to reduce mutual coupling between adjacent loops 22, according to techniques known in the art. The antenna arrays 20 are mounted to a flexible, thin film substrate 28, for example KAPTON®, such that the substrate 28 may be flexed in an arcuate manner, the curvature of the substrate 28 preferably following the rows of antenna loops 22. A pick-up circuit 24 is joined to each antenna loop 22, for example by soldering. A conductor 26 is also connected to the each pick-up circuit 24 for transmitting the signal received by the antenna loop 22. Each conductor 26 is routed together to form a cable 32. The cable 32 is preferably pre-terminated to a single connector 30, such that each antenna array 20 may be quickly connected or disconnected as a single unit in the imaging receiver 10. The modular nature of the antenna arrays 20 allows multiple antenna arrays 20 to be used according to, for example, the requirements of a particular anatomical region to be imaged or the number of channels required by the MRI system.

Figure 10:
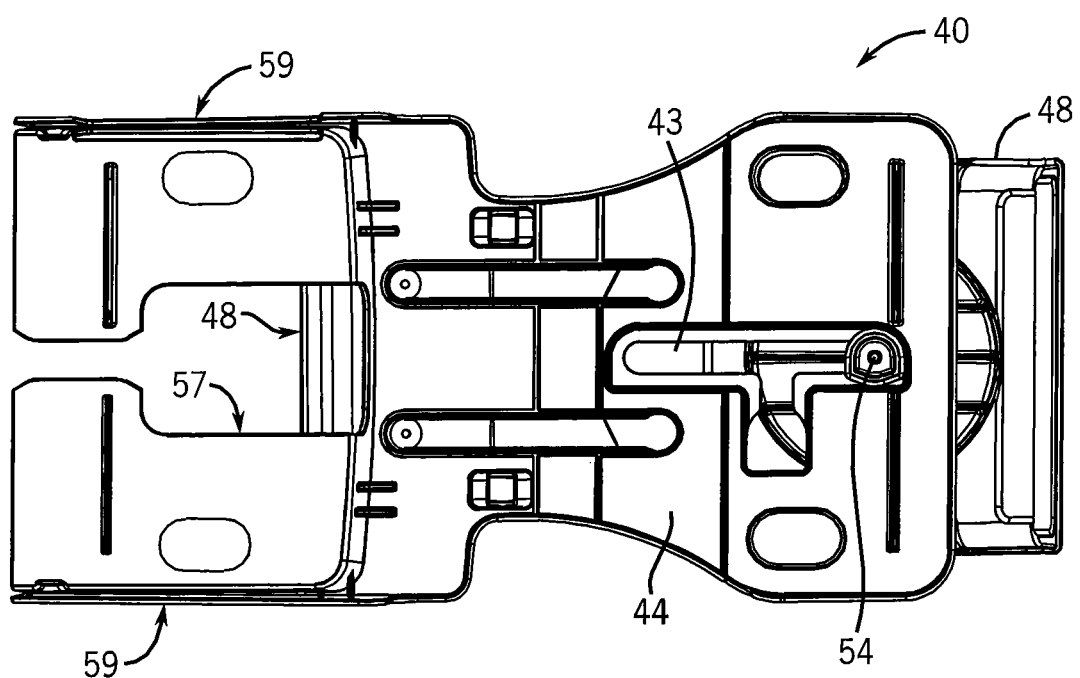
FIG. 10 is a bottom plan view of the patient stabilization device of FIG. 4.
Figure 11:
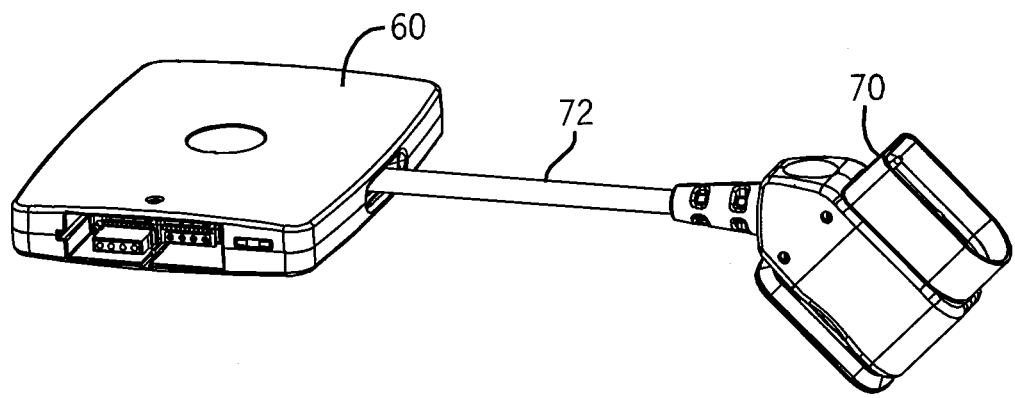
FIG. 11 is an isometric view of the preamplifier module of FIG. 4.

Referring also to FIG. 10, the preamplifier module 60 includes, in part, the electronic components associated with the preamplifier circuits of each antenna loop 22, which have commonly been included within the housing used to hold the antenna coils. Dividing these electronic components into a separate module reduces the number of electronic components required to be mounted to the antenna arrays 20 and facilitates providing separate antennae arrays 20 and patient support structures. Optionally, the preamplifier circuits may be divided into sections and supplied in part on the antenna array 20 and in part within the preamplifier module 60. Similarly, the entire preamplifier circuit may still be provided on the antenna array 20. It is further contemplated that a portion of the circuit may be provided within the cable 32 or connector 30 as a cable assembly (not shown). Further, the preamplifier module 60 may auto-configure itself, described below, and may bypass a portion or all of the preamplifier circuitry contained within the preamplifier module if duplicate circuitry exists on the antenna array 20 or within the cable assembly.

The preamplifier module 60 can auto-configure itself according to the devices connected to it and perform initial processing on the signals received from the antenna arrays 20 prior to passing the signals to the MRI scanner. The preamplifier module 60 initially detects the components connected to it using a processor executing a stored program and information stored on a memory device connected to the processor. For example, each antenna array 20 may be assigned a unique identifier and provide a signal to the preamplifier module 60 indicative of this identifier. The program may then access the memory device to determine the attributes of the antenna array 20, such as the number of loops 22, within with the antenna array 20.

Similarly, each stabilization structure 40 may be configured to provide an identifier to the preamplifier module 60. For example, an additional connector may be included on the preamplifier module 60 which engages a corresponding connector on the stabilization structure 40. The support structure ID may be passed using this additional connector. Alternately, a series of switches may be mounted on the preamplifier module 60. Each stabilization structure 40 may engage the preamplifier module 60 such that a different combination of switches is engaged for each stabilization structure 40. Alternately, any means known in the art may be used to provide a support structure ID to the processor in the preamplifier module 60.

As still another step in the auto-configuration process, the preamplifier module 60 interfaces with the MRI scanner to determine the number of channels available on the MRI scanner. The preamplifier module 60 then determines how to process the signals from the antenna arrays 20 according to the number of input channels, the anatomical region being imaged, and the number of channels available on the MRI scanner. For example, the preamplifier module 60 may permit signals to simply pass through from the antenna loop 22 to the MRI scanner. Alternately, the preamplifier module 60 may configure switching and combination logic to read signals from the appropriate set of antenna arrays 20. The preamplifier module 60 may arrange signals from multiple arrays 20 to provide a single array of signals with a higher number of channels to the MRI scanner. In this manner, the preamplifier module 60 may facilitate using multiple antenna arrays 20 to scan a FOV beyond the size of a single antenna array 20. Alternately, the preamplifier module 60 may also be used to convert the number of channels available from the coil arrays 20 to the number of channels available on the MRI scanner. For example, the combined number of channels from each of the coil arrays 20 connected to the preamplifier module 60 may be greater than the number of channels available on the MRI scanner. The preamplifier module 60 can combine the signals input from the coil arrays 20 to output the appropriate number of channels to the MRI scanner.

As still another aspect of the invention, multiple preamplifier modules 60 may be used in cooperation with multiple antenna arrays 20 to provide the output signals to the MRI scanner. Each preamplifier module 60 may receive input signals from one or more antenna arrays 20 as required by the imaging applications. An output cable 72 and connector 70 may be provided to connect each preamplifier module 60 to the MRI scanner.

Figure 22:
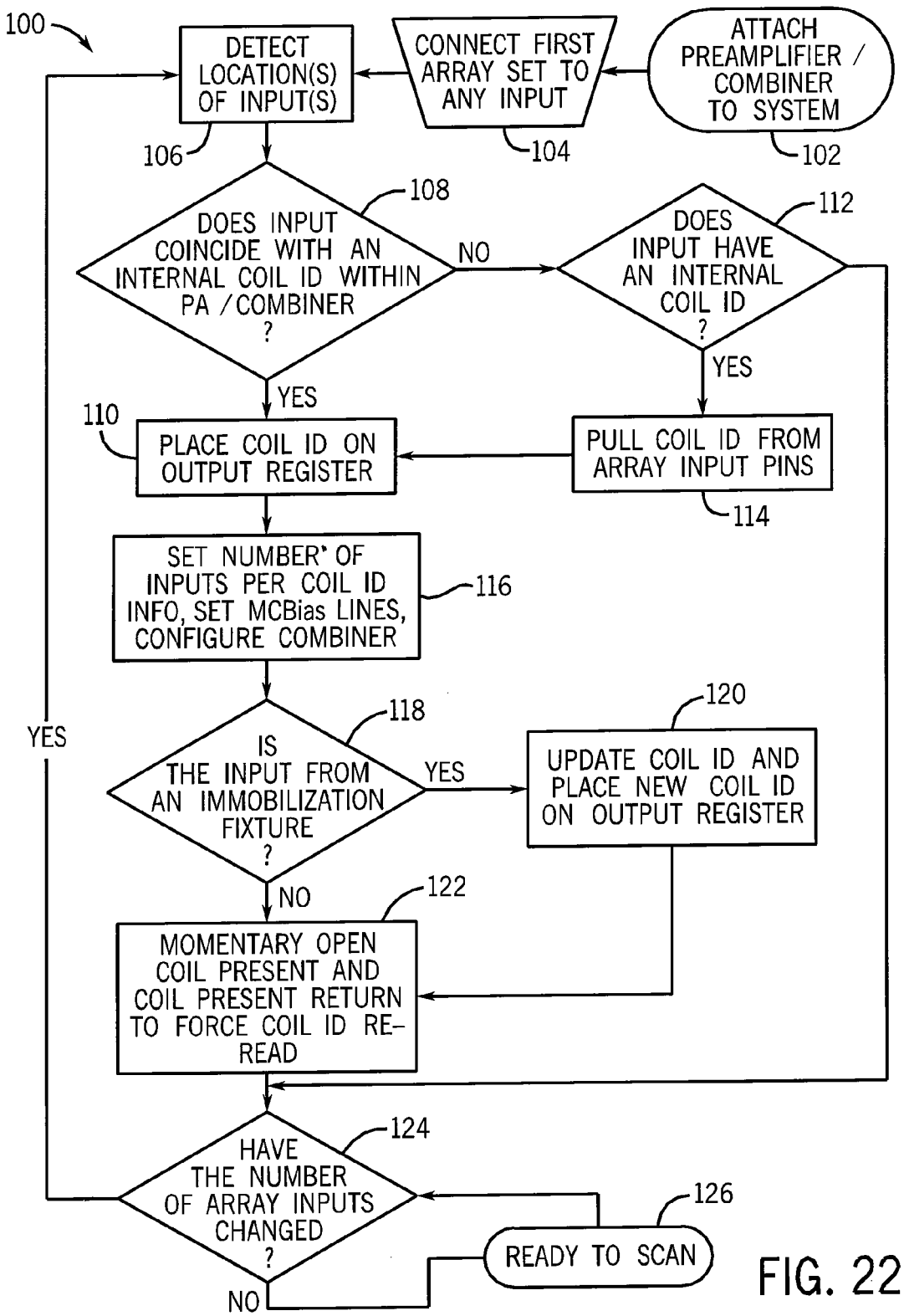
FIG. 22 is a flowchart showing the steps performed by the preamplifier module for auto detection of an antenna array at the input connector.

Referring to FIG. 22, a flowchart 100 illustrating, in part, the automatic configuration of the preamplifier module 60 is disclosed. The preamplifier module 60 is first connected 102 to the MRI scanner using a cable between at least one, and preferably each, of the output connectors 66 of the preamplifier module 60 and the MRI scanner connectors. An antenna array 20 is connected 104 to one of the input connectors 64 on the preamplifier module 60. The preamplifier module 60 detects 106 the presence of an array 20 at each of the input connectors 64 having an antenna array 20 connected. The preamplifier module then determines 108 whether a new antenna array has been added to the system. If no new antenna array has been added, the antenna array IDs previously detected are read 110 from memory and moved to an output register.

If a new antenna array 20 is identified at one of the input connectors 64, the preamplifier determines 112 whether the new array 20 has an array ID. If the antenna array 20 does not have a valid array ID or the preamplifier module 60 is unable to read the array ID, then the preamplifier module 60 indicates to the MRI scanner that it is not ready to begin imaging. If the antenna array 20 has an array ID, the preamplifier module 60 reads 114 the array ID from the new device, and that array ID is moved 110 to the output register. The preamplifier module sets 116 the number of input channels according to the array ID information and configures the combiner within the preamplifier module 60. The combiner may be configured to parallel process multiple images, combine multiple arrays into a single image, pass channel information directly to the MRI scanner, or convert the input channels to the appropriate number of output channels for the MRI scanner.

The preamplifier module 60 next determines whether the new device includes a patient stabilization structure 40. If the new device is a patient stabilization structure 40, the array ID is updated 120 to indicate that a new patient stabilization structure 40 has been connected. After updating the array ID or if the new device was not a patient stabilization structure 40, the preamplifier module 60 then reinitiates 122 reading all of the coil ID information. If no changes 124 have been made to the inputs to the preamplifier module 60 and no unidentified devices have been detected, the preamplifier module 60 indicates 126 to the scanner that it is ready to scan. If the number of inputs to the preamplifier module 60 changed, the process of identifying what antenna arrays 20 are connected and configuring the preamplifier module 60 is repeated.

Different MRI scanners have different requirements for identifying which antenna arrays 20 are connected to the preamplifier module 60 and, ultimately, to the MRI scanner. The preamplifier module 60 may be configured to communicate to different MRI scanners to properly identify the type and number of antenna arrays 20 connected to the preamplifier module 60. For example, the memory device in the preamplifier module 60 may include a second table of coil IDs that properly identify the antenna arrays 20 for different MRI scanners. The second coil ID may subsequently be passed to the MM scanner. Alternately, the preamplifier module 60 may include one or more additional connectors to either directly provide identifying electrical signals to the MRI scanner or to pass identifying signals through from the antenna arrays 20 to the MM scanner.

The preamplifier module 60 may additionally be used to help configure the MRI scanner. By sending the IDs of the coil arrays 20 and the patient stabilization structures 40 to the MM scanner, the MRI scanner is able to present the proper scanning protocols to the technician according to the imaging system that is connected to the scanner.

The preamplifier module 60 can also be used to detect the number of times a specific antenna array 20 has been connected to the preamplifier module 60. This function enables the pre-amplifier module 60 to detect if an antenna array 20 has been used in excess of a contracted number of uses or expected lifetime.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention

We claim:

1. A magnetic resonance image (MRI) receiver for detecting a plurality of nuclear magnetic resonance (NMR) signals and for transmitting the NMR signals to a MRI scanner, comprising:
   at least one antenna array, each antenna array further comprising a flexible substrate and a plurality of antennae mounted on the substrate;
   a cable having a plurality of electrical conductors corresponding to one of the antennae;
   a preamplifier module having at least one input connector and at least one output connector, the input connector configured to receive the cable to connect the preamplifier module to the antenna array and the output connector configured to connect the preamplifier module to the MRI scanner.

2. The MRI receiver of claim 1 wherein the antenna array further comprises a pick-up circuit mounted on the substrate to transfer the NMR signal received on each antenna to the corresponding electrical conductor.

3. The MRI receiver of claim 1 wherein the antenna array is generally rectangular and may be selectively positioned in a generally planar first state or a generally arcuate second state.

4. The MRI receiver of claim 3 further comprising a spacer block extending between a first edge and a second edge of the antenna array at a first end of the antenna array, wherein the spacer block is configured to be on the outer surface of the antenna array when the antenna array is in the second state and is configured to engage the inner surface of a second end of the antenna array overlapping the first end of the antenna array such that the second end of the antenna array is positioned at an angle to the first end of sufficient magnitude to minimize coupling between overlapping antennae.

5. The MRI receiver of claim 1 wherein a first antenna array is connected to a first input connector on the preamplifier module and a second antenna array is connected to a second input connector on the preamplifier module.

6. The MRI receiver of claim 5 wherein the preamplifier module combines the signals from the first and second antenna arrays into a combined output transmitted to the MRI scanner.

7. The MRI receiver of claim 1 wherein the antenna array includes at least one antenna having a first size and at least one antenna having a second size.

8. The MRI receiver of claim 1 wherein the preamplifier module further comprises:
   a processor configured to receive input signals from the input connector and to transmit output signals to the output connector; and
   a memory device storing processor executable instructions, wherein the instructions are executable to detect each antenna array connected to one of the input connectors and to determine the number of antennae on each antenna array.

9. The MRI receiver of claim 8 wherein the instructions are further executable to detect the MRI scanner connected to the output connector and to convert the input signals to the appropriate output signals according to the MRI scanner detected.

10. The MRI receiver of claim 1 further comprising a stabilization structure including a base plate and a support member adjustably positioned on the base plate.

11. The MM receiver of claim 10 wherein the stabilization structure further comprises:
   a first mounting surface to which a first end of the antenna array is removably connected; and
   a second mounting surface to which a second end of the antenna array is removably connected, wherein an angle formed between the first mounting surface and the second mounting surface is of sufficient magnitude to minimize coupling between overlapping antennae.

12. The MRI receiver of claim 10 further comprising a shield for radiated emissions removably connected to the stabilization structure.

13. The MRI receiver of claim 12 wherein the shield is a radio frequency (RF) blanket, further comprising:
   at least one conductive layer configured to prevent RF signals from radiating therethrough;
   a flexible outer layer substantially covering the conductive layer; and
   a fastener attached to the outer layer for connecting the RF blanket to the stabilization structure.

14. The MRI receiver of claim 13 wherein the RF blanket further comprises at least one absorbing layer covering one of the conductive layers and wherein the conductive layer is one of a sheet or a mesh material.

15. The MRI receiver of claim 10 wherein the preamplifier module is removably connected to the stabilization structure.

16. A magnetic resonance image (MRI) receiver for receiving a plurality of nuclear magnetic resonance (NMR) signals and for transmitting the NMR signals to a MRI scanner, comprising:

a stabilization structure including a base plate and a support member adjustably positioned on the base plate;

at least one antenna array removably connected to the stabilization structure, each antenna array further comprising a flexible substrate and a plurality of antennae mounted on the substrate;

a preamplifier module having at least one input connector and at least one output connector, the input connector configured to connect the preamplifier module to the antenna array and the output connector configured to connect the preamplifier module to the MRI scanner; and at least one cable electrically connecting the antenna array to the preamplifier module and having a plurality of electrical conductors corresponding to one of the antennae.

17. The MRI receiver of claim 16 further comprising a second stabilization structure adjustably positioned on the base plate.

18. The MRI receiver of claim 17 further comprising a shield for radiated emissions removably connected to the second stabilization structure.

19. The MRI receiver of claim 18 wherein the shield is a radio frequency (RF) blanket further comprising at least one conductive layer configured to prevent RF signals from radiating therethrough;

a flexible outer layer substantially covering the conductive layer; and a fastener attached to the outer layer for connecting the RF blanket to the second stabilization structure.

20. The MRI receiver of claim 16 wherein the stabilization structure further comprises:

a first mounting surface to which a first end of the antenna array is removably connected; and a second mounting surface to which a second end of the antenna array is removably connected, wherein the first and second mounting surfaces are configured to maintain a separation between the first end and the second end of the antenna array of sufficient magnitude to minimize coupling between overlapping antennae.

* * * * *